United States Patent [19]

Bouillant et al.

[11] Patent Number: 5,112,756
[45] Date of Patent: May 12, 1992

[54] CONTINUOUS PRODUCTION OF BOVINE MAEDI-VISNA-LIKE VIRAL ANTIGENS IN CF2TH CELLS

[75] Inventors: Alain M. P. Bouillant, Aylmer; Klaus Nielsen, Richmond; Gerda M. Ruckerbauer; Bakhshish S. Samagh, both of Nepean; William C. D. Hare, North Gower, all of Canada

[73] Assignee: Canadian Patents and Development Limited, Canada

[21] Appl. No.: 57,213

[22] Filed: Jun. 1, 1987

[30] Foreign Application Priority Data

Jun. 2, 1986 [CA] Canada ................................ 510622

[51] Int. Cl.$^5$ .......................... C12N 7/00; C12N 7/02; C12N 5/10
[52] U.S. Cl. .............................. 435/235.1; 435/239; 435/240.1; 435/240.2; 435/240.25; 435/948
[58] Field of Search ............ 435/235, 239, 948, 240.2, 435/68, 235.1, 240.1, 240.24, 240.25, 70.1, 70.4; 424/89

[56] References Cited

U.S. PATENT DOCUMENTS

| | | | |
|---|---|---|---|
| 3,432,595 | 3/1960 | Kasza | 435/239 |
| 3,520,972 | 7/1970 | Smith | 424/89 |
| 3,590,127 | 6/1971 | Bryans et al. | 424/89 |
| 3,873,690 | 3/1975 | Rand | 424/89 |
| 4,323,555 | 4/1982 | Theilen | 435/240.27 |
| 4,647,773 | 3/1987 | Gallo et al. | 435/239 |
| 4,721,675 | 1/1988 | Chan et al. | 435/948 |
| 4,729,955 | 3/1988 | Kodama et al. | 435/948 |

OTHER PUBLICATIONS

Elder et al., Journal of Virology 61(1) pp. 8-15 (1987).
Tateno, et al., Journal of Experimental Medicine 159, pp. 1105-1116 (1984).
Graves et al., Cancer Research 36, pp. 4152-4158 (1976).
In vitro Host Range of Equine Infectious Anemia Virus, Intervirology 16:225-232 (1981) C. V. Benton et al.
Equine Infectious Anemia Vaccine, Animal Models of Retrovirus Infection and their relationship to AIDS, pp. 387-392 Academic Press (1986), D. T. Shen.
Nontumoral, Benign and Malignant Stages of Transformation of a Diploid Pig Cell. A Review, Can. J. comp. Med. 45, 279-290 (Jul. 1982), A. M. P. Bouillant et al.
Attempts to Isolate Bovine Leukemia and Bovine Syncytial Viruses from Blood, Uterine Flush Fluid, Unfertilized Ova and Embryos from Infected Donor Cattle, Ann. Rech. Vet. 12(4), 385-395 (1981), A. M. P. Bouillant et al.
Ultrastructural Comparison of Oncovirinae (Type C), Spumavirinae, and Lentivirinae:Three Subfamilies of Retroviridae found in Farm Animals, J.N.C.I. 72 (5), 1075-1084 (May 1984), A. M. P. Bouillant et al.

Primary Examiner—Elizabeth C. Weimar
Assistant Examiner—Gail Poulos
Attorney, Agent, or Firm—Kenyon & Kenyon

[57] ABSTRACT

Permanent infection of a cell line such as a canine thymus cell line with a retrovirus such as equine infectious anemia virus and bovine Maedi-Visna-like virus is now possible. By culturing such an infected cell line under appropriate conditions, it is now possible to produce large quantities of viral antigens on a continuous basis. Such antigens are useful in for diagnostics and research.

7 Claims, 4 Drawing Sheets

CONTINUOUS PRODUCTION OF BOVINE MAEDI-VISNA-LIKE VIRAL ANTIGENS IN CF2TH CELLS

BACKGROUND OF THE INVENTION

This invention is concerned with the production of viral antigens by persistently infected cell lines and the use of such antigens for diagnostic and other purposes.

U.S. Pat. No. 3,590,127 (issued: Jun. 29, 1971; inventors: J. T. Bryans et al) is concerned with a process for producing equine viral arthritis vaccine. U.S. Pat. No. 3,520,972 (issued: Jul. 20, 1970; inventors: S. E. Smith et al) is concerned with feline virus Vaccines obtained by propagation and serial passage attenuation of virulent feline viruses in diploid feline embryo tissue cell serial passage subculture strains. U.S. Pat. No. 3,432,595 (issued: Mar. 11, 1969; inventor: L. Kasza) is concerned with a canine melanoma cell line and its propagation and use for producing vaccines. A process for producing an equine infectious anemia vaccine, for use in immunizing horses, from organs of sick horses is described and claimed in U.S. Pat. No. 3,873,690 (issued: Mar. 25, 1975; inventor: J. H. Rand III).

Equine infectious anemia (EIA) is a viral disease that occurs naturally in members of the horse family. It is characterized by a diversity of symptoms and may appear in acute, subacute or chronic forms. It was reported first in Europe in 1843 and subsequently about 1880 as a specific disease in Canada.

Equine infectious anemia virus (EIAV) is a retrovirus belonging to the lentivirus subfamily. It contains two glycoproteins (gp70 and gp45) and four major non-glycosylated proteins (p26, p15. p11 and p9). It can cross-react with other retroviruses; for example, sera of EIAV-infected horses precipitated the p25 protein of a retrovirus (LAV or HTLV-III) and a lentivirus associated with acquired immune deficiency syndrome (AIDS) of man.

To date, usually, in vitro EIAV replication for antigen production has been limited to primary cells or diploid finite cell lines. This hampered antigen production because there were repetitive demands for cell stocks and it was necessary to continually screen primary cells for infectious contaminants.

Consequently, if one succeeds in growing EIAV in tumor cells as partially demonstrated using different techniques by Benton et al. Intervirol. 16, 225-232, (1981), but also succeeds in producing a persistently infected potentially infinite cell line, the above restrictions applying to diploid cells can be eliminated and high yields of viral antigens can be expected since malignant cells generally grow at a higher saturation density than diploid cells.

In order that a permanent and productive infection be of use for continuous and large-scale production of antigens the following key problems have to be addressed:

(1) the infection must be made persistent;

(2) antigen release must be continuous;

(3) the cell line must be capable of an indefinite (preferably infinite) life;

(4) a culture system must be developed which allows the production, harvesting and purification of antigens.

By analogy, the infected cell line should be comparable to hybridoma cells releasing monoclonal antibodies.

We believe that we have now achieved this end and can report the persistent EIA infection in a malignantly-transformed canine thymus cell line, Cf2Th, ATCC CRL 1430 and the continuous release of viral antigens for more than 200 serial passages. Furthermore, preliminary data are presented on the production of viral antigens in roller bottles since the EIAV-infected Cf2Th cell cultures release viral antigens in the supernatant fluid.

SUMMARY OF THE INVENTION

According to the present invention, there is provided a malignantly transformed cell line, infected with a virus, the cells of which cell line are capable of continuously reproducing themselves and of continuously producing viral antigen for at least 25 passages.

Preferably such a cell line is derived from canine thymus cells, especially canine thymus cells of the Cf2Th type, and has a capacity for continuously producing viral antigen for 50, 100, 150, or, most preferably, at least 200 passages.

The virus is preferably a retrovirus and may be equine infectious anemia virus. Other preferred viruses are members of the group: bovine leukemia virus, bovine syncytial virus, Maedi-Visna virus, caprine arthritis encephalitis virus, feline T lymphotropic lentivirus, bovine Maedi-Visna-like virus, equine infectious anemia virus, HTLV-I, II, LAV/HTLV-III, HTLV-IV and simian-TLV. It may be preferred that the virus is an oncovirus, a spumavirus or a lentivirus.

Preferably such a cell line is a malignantly transformed canine thymus cell line Cf2Th infected with equine infectious anemia virus, the cells of said cell line being capable of continuously reproducing themselves and of continuously producing viral antigen for at least 200 passages. An especially preferred embodiment employs the AICC CRL 1430 cell line.

In another aspect of the invention there is provided a method of continuously producing a viral antigen which comprises culturing the above-referenced cell line under conditions conducive to the production of said viral antigen.

A preferred method of continuously producing a viral antigen from a malignantly transformed cell infected with a virus, cells of said cell line being capable of continuously reproducing themselves and of continuously producing viral antigens for at least 25 passages, comprises culturing cells of said line in fluid medium under conditions conducive to the production of said antigen to allow said antigen to be produced in the fluid medium, harvesting, when required, an aliquot of said fluid medium and isolating said antigen from said aliquot to yield a purified antigen.

A preferred embodiment of this aspect is a method of continuously producing an equine infectious anemia virus antigen from a malignantly transformed canine thymus cell line infected with equine infectious anemia virus, cells of said cell line being capable of continuously reproducing themselves and of continuously producing said antigen for at least 25 passages which comprises culturing cells of said cell line in fluid medium under conditions conducive to the production of said antigen to allow said antigen to be produced in the fluid medium, harvesting, when required, an aliquot of said fluid medium and isolating said antigen from said aliquot to yield a purified antigen. Especially preferred is such a method which employs a Cf2Th cell line infected with equine infectious anemia virus.

In a further aspect of this invention there is provided a kit for detecting the presence in a sample of a virus having an epitope in common with a virus selected from the group consisting of a bovine leukemia virus, bovine syncitial virus, Maedi-Visna virus, caprine arthritis encephalitis virus, feline T lymphotropic lentivirus, bovine Maedi-Visna-like virus, equine infectious anemia virus, HTLV-I, II, LAV/HTLV- III, HTLV-IV and simian-TLV which kit comprises: (a) an antigen of said virus; (b) detection means whereby an antibody in the sample, when linked to said antigen, may be indicated.

A preferred embodiment of this aspect of the invention comprises a kit for detecting the presence in a sample of a virus having an epitope in common with equine infectious anemia virus which comprises: (a) an antigen of said virus; (b) detection means whereby an antibody in the sample, when linked to said antigen, may be detected.

In such kits detection means: preferably comprises a radio active label, a fluorescent label or an enzyme label. Especially preferred is an immunoglobulin, capable of binding to the antibody, labelled with horseradish peroxidase. In some embodiments of such kits the antigen may be attached to a solid phase substrate.

In some embodiments such a kit may further comprise a cross-linking agent, such as glutaraldehyde or formalin to enhance antibody or antigen immobilization.

In a further aspect of this invention there is provided a method for detecting the presence of a virus selected from the group consisting of bovine leukemia virus, bovine syncytial virus, Maedi-Visna virus, caprine arthritis encepalitis virus, feline T lymphotropic lentivirus, bovine Maedi-Visna-like virus, equine infectious anemia virus, HTLV-I, II, LAV/HTLV-III, HTLV-IV and simian TLV which comprises: exposing a sample from an animal suspected of having been infected with one of said viruses or suspected of carrying an antibody to one of said viruses to an antigen of the virus suspected to have infected said animal, to allow an antibody in said sample to contact said antigen; and detecting the presence of antibody linked to the antigen.

In some embodiments it maybe preferred to attach the antibody in the sample to a solid substrate.

In some other embodiments it may be preferred to attach the antigen to a solid substrate.

In other embodiments labels or cross-linking agents of the type optionally employed in kits of the invention may be employed.

A preferred embodiment of this aspect of the invention comprises a method for detecting the presence of equine infectious anemia virus which comprises: exposing a sample from an animal suspected of having been infected with said virus or suspected of carrying an antibody to said virus to an equine infectious anemia virus antigen to allow an antibody in said sample to contact said antigen; and detecting the presence of antibody linked to the antigen.

Another preferred embodiment comprises a method for detecting a virus having an epitope in common with a virus selected from the group consisting of bovine leukemia virus, bovine syncytial virus, Maedi-Visna virus, caprine arthritis encephalitis virus feline T lymphotropic lentivirus, bovine Maedi-Visna-like virus, equine infectious anemia virus, HTLV-I HTLV-II, LAV/HTLV-III, HTLV-IV and simian-TLV which comprises: (a) exposing a sample from an animal suspected of having been infected with said virus having said epitope or suspected of carrying an antibody to said virus with said epitope to an antigen of a virus selected from the group consisting of bovine leukemia virus, bovine syncytial virus, Maedi-Visna virus, caprine arthritis encephalitis virus, feline T lymphotropic lentivirus, bovine Maedi-Visna-like virus, equine infectious anemia virus,HTLV-I, HTLV-II, LAV/HTLV-III, HTLV-IV and simian-TLV, to allow an antibody in said sample to contact said antigen; and detecting the presence of antibody linked to the antigen.

A further preferred embodiment of this aspect of the invention may comprise a method for detecting LAV/HTLV-III virus using an equine infectious anemia virus antigen which comprises: (a) exposing a sample from a subject suspected of containing LAV/HTLV-III virus or suspected of carrying an antibody to an LAV/HTLV-III virus; to an equine infectious anemia virus antigen to allow an antibody in said sample to contact said antigen; and detecting the presence of antibody linked to the antigen.

DESCRIPTION OF THE DRAWINGS

In the drawings which illustrate embodiments of the invention.

DETAILED DESCRIPTION OF THE INVENTION

1. Establishment of persistent EIAV infection in vitro

A 75 cm$^2$ flask of Cf2Th-59 (59th cell passage) cells were treated for 50 minutes with 25 g/DEAE-Dextran/ml. The mono-layer was then washed once and inoculated with 15 ml of supernatant fluid from the 50th passage on embryonic mule skin (EMS) diploid cells of the Wyoming EIAV strain (The EMS/EIA cell line was obtained from National Animal Disease Center, U.S. Dept. of Agriculture, Ames, Iowa, U.S.A.) which had been filtered through a 0.22 μm filter unit (Millex*-H.A., Millipore Corp., Bedford, Mass., U.S.A.). Five days after inoculation, the cells were divided 1:3 and thereafter 1:4 every 5–7 days for the first 30 virus passages and 1.5 every 3–4 days for subsequent passages. Complete Dulbecco minimum essential medium (D-MEM) medium supplemented with 10% fetal bovine serum (FBS) and antibiotics was used throughout.

Both control and EIAV-infected cells were monitored for the presence of EIAV during 100 serial passages by electron microscopy, direct immunofluorescence and immunodiffusion.

Virus isolation and titration from EIAV-infected Cf2Th cells were made on DEAE-Dextran treated fetal equine choroid plexus cells and presence of viral antigens was demonstrated by immunofluorescence. Choroid plexus cells were prepared by standard explant technique.

Cell growth curves were determined in growing uninfected and EIAV-infected Cf2Th cells in 25 cm$^2$ plastic flasks and counting cells daily in duplicate with an improved Neubauer* hemocytometer. Cell cultures were also tested for mycoplasma and bacterial contaminants.

Evidence of the persistent EIAV infection

Data demonstrating the persistent infection are shown in Table 1.

A few EIA virions were observed at the 3rd, 5th, 7th and 19th days of the Cf2Th-63/EIAV-5 passage and continuously thereafter in subsequent passages. Budding viruses and complete virions were observed by electron-microscopy on cell membranes and in intercellular spaces, while EIAV-associated structures in proximity to the endoplasmic reticulum were encountered most frequently in the cytoplasm. An inverse relationship seemed to occur in the Cf2Th-83/EIAV-25 passage between the relative amount of cytoplasmic viral structures and both budding and mature viruses, and, peak of the former at days 3-5 and the latter at days 9-11 after trypsinization although no formal evaluation was made. Neither EIA virions nor other viral contaminants were observed in noninfected control cells. Morphological cell alterations were not observed in EIAV-infected and control Cf2Th cells by the phase contrast microscopy with the exception of an increase of cytoplasmic vacuolization with increased passages of EIAV-infected cells.

Figure 1:
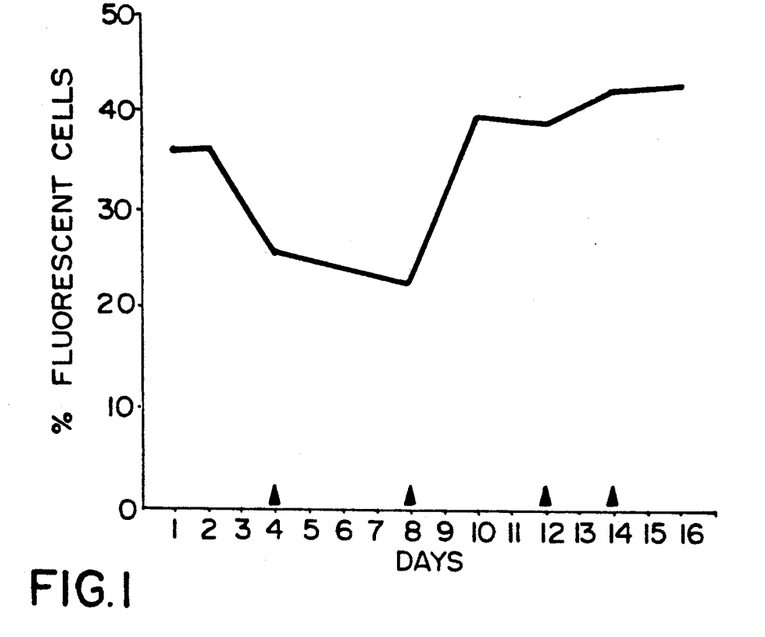
FIG. 1 shows the percentage of EIAV-fluorescent cells of the Cf2Th-104/EIAV-46 passage for 16 days (the arrows indicate medium change) against time.
Figure 2:
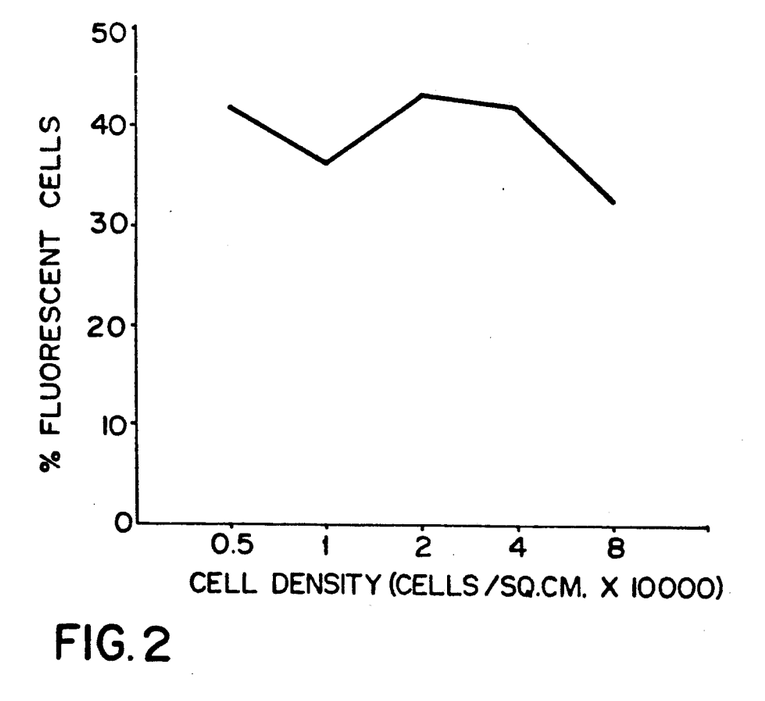
FIG. 2 shows the percentage of EIAV-fluorescent cells 24 hours after seeding the Cf2Th-110/EIAV-52 passage, plotting percentage fluorescent cells against cell density.

Weak immunofluorescence was observed when first tested at the Cf2Th-63/EIAV-5 passage, while stronger fluorescence was noted in clusters of cells of the Cf2Th-65/EIAV-7 passage (Table 1). Specific EIAV fluorescence was not observed in noninfected-control cells. FIG. 1 gives a range of 22.6 to 43% of positive immunofluorescent cells when 5×10$^3$ cells of the Cf2Th-104 EIAV-46 passage were seeded and examined every other day for 16 days. FIG. 2 gives the percentage of EIAV fluorescent cells when those of the Cf2Th-110/EIAV-52 passage were seeded at different densities and examined 24 h after seeding. The maximum and the minimum of positive immunofluorescent cells were observed at density of 2×10$^4$ and 8×10$^4$ cells/cm$^2$, respectively.

Ether-extracted antigens from the supernatant fluids of EIAV-infected cells gave a clear positive reaction at the 11th virus passage and thereafter (Table 1) in the immunodiffusion test. Lines of identity corresponding to a known positive EIAV antigen extracted from EIAV-infected equine spleen and a commercial antigen (Pitman-Moore, Washington Crossing, N.J.) were demonstrated. No reaction was seen from supernatant fluids of noninfected control cells.

Figure 3:
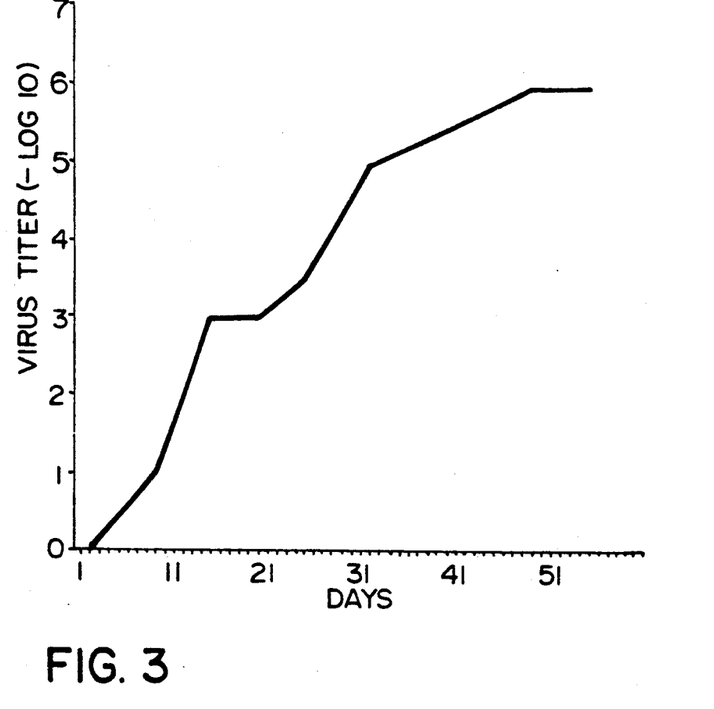
FIG. 3 is a plot of virus titer against time when 1 ml of supernatant fluid was inoculated in duplicate per 25 cm$^2$/flask of choroid plexus culture.

EIAV from supernatant fluids of the Cf2Th-111/EIAV-53 and Cf2Th-115/EIAV-57 passages were adsorbed for 4 hours on DEAE-Dextran-treated fetal equine choroid plexus cells. EIAV antigens were detected by direct immunofluorescence in the 3rd serial virus passage, i.e., 18 days post primary inoculation of equine choroid plexus cells for the Cf2Th-111/EIAV-53 passage and 10 days post primary inoculation of equine choroid plexus cells for the Cf2Th-115/EIAV-57 passage. This last passage was titrated on equine choroid plexus cells (FIG. 3). Neither cytopathic effect nor changes of cellular morphology were observed in either EIAV-infected or noninfected equine choroid plexus cells when the cells were routinely examined by the phase contrast microscopy or stained by the May-Grünwald stain. Mycoplasmal or bacterial contaminants were not isolated when cells were tested at different passages (Table I).

Figure 4:
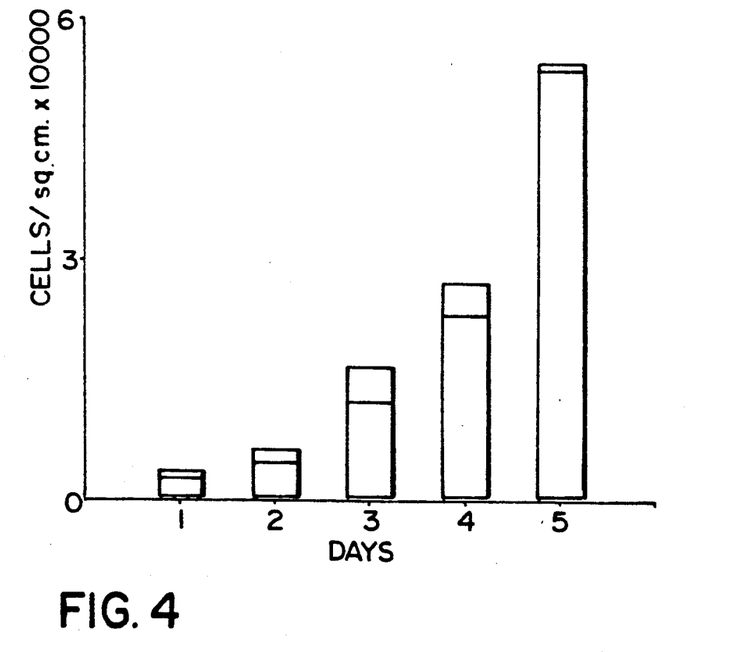
FIG. 4 shows comparative growth curves of control (Cf2Th-117-open frame) and EIAV-infected cells (Cf2Th-112-slashed frame)

A preliminary observation at the Cf2Th-112/EIAV-54 suggested that EIAV-infected cells might have had a growth rate slightly less than noninfected control cells (Cf2Th-117) (FIG. 4). Control cells had a population doubling time 11.5% shorter than the EIAV-infected cells.

TABLE 1

| | Evidence of the permanent EIAV infection of the Cf2Th cell line | | | | |
|---|---|---|---|---|---|
| Virus passage | Electron microscopy | Immunofluorescence | Immunodiffusion | EIA isolation | Mycoplasma testing |
| 1-10 | +(5)[a] | ±(5), +(7,10) | n.t.[a] | n.t. | n.t. |
| 11-20 | +(13) | +(11,17,20) | +(11,12,13) | n.t. | −(18) |
| 21-30 | +(25) | +(22,29) | n.t. | n.t. | n.t. |
| 31-40 | n.t. | +(38) | +(32,33,36) | n.t. | n.t. |
| 41-50 | +(41) | +(46) | n.t. | n.t. | n.t. |
| 51-60 | +(57,60) | +(51) | +(59) | +(53,57)[b] | −(56) |
| 61-70 | n.t. | +(68) | +(63,64,70) | n.t. | −(63) |
| 71-80 | n.t. | +(79) | +(72) | n.t. | n.t. |
| 81-90 | n.t. | n.t. | +(81) | n.t. | n.t. |
| 91-103 | +(94) | +(92,103) | +(91,102) | n.t. | −(92) |
| 104-150 | n.t. | +(126,128,144) | n.t. | n.t. | n.t. |
| 150-200 | +(165) | +(152,185,200) | n.t. | n.t. | n.t. |

[a] + or −: positive or negative reaction; n.t.: not tested;
( ): virus passage number.
[b] Virus isolation made in equine choroid plexus cells.

2. Production of EIAV antigens in roller bottles

EIAV antigens were produced by seeding approximately 1×10$^7$ cells (2×10$^4$ cells/cm$^2$) in 100 ml of medium per 490 cm$^2$ roller bottle which was then incubated at 37° C. The medium used was Earle's MEM, supplemented with 10% FBS, 400 mM glutamine, 10 mM non-essential aminoacids, 25 mM Hepes, 100 μg gentamycin/ml and 60 μg tylosin/ml. The pH was adjusted to 7.3-7.4 with 7.5% sodium bicarbonate. The cells were maintained continuously for 65 days at 0.19 rpm without subculturing.

Supernatant fluids to be tested for presence of EIAV antigens were harvested every 3-4 days for 65 days and replaced by 50 ml of fresh medium. Harvested supernatant fluids were centrifuged at 130×g for 10 min to remove cells and debris and concentrated 4× in the Pellicon TM cassette system (exclusion M.W. 10.000 dalton; Millipore Corp., Bedford, Mass., U.S.A.). The concentrated supernatant fluid was precipitated by polyethylene glycol (M.W. 6.000 dalton) to final concentration of 89 times the original volume and EIAV antigens were extracted by treatment with anhydrous ether. Immunodiffusion, radial immunodiffusion and rocket immunoelectrophoresis were performed every 3–4 days for 65 days.

To remove most of the bovine proteins, an alternate procedure was used to concentrate and purify the ether-extracted antigen. Supernatant fluid was centrifuged at 10,000×g for 15 min at 4° C. It was concentrated 10-fold with the Pellicon cassette system or the XM50 Amicon TM membrane (exclusion M.W. 50,000 dalton; Amicon Corp., Lexington, Mass., U.S.A.). The concentrated fluid was precipitated with 27 gm $(NH_4)_2SO_4$ per 100 ml of fluid and stirred at room temperature for 15 min. The precipitate was recovered by centrifugation at 10,000×g for 15 min at 4° C. and resolubilized in a minimum amount of distilled water. Then it was treated with an equal volume of anhydrous ether with vigorous shaking for 1 h and allowed to stand until partition occurs. The ether layer was removed by suction and the aqueous part was dialysed against distilled water (10 volumes minimum×2 changes over 24 h). Insoluble materials resulting from dialysis were removed by centrifugation (10,000×g for 15 min at 4° C.). The antigen which was in the supernatant fluid was adjusted for immunodiffusion tests either by dilution or concentration pressure dialysis using a XM10 Amicon membrane. Ninety-five percent of the bovine proteins were removed by this method.

Concentrated supernatant fluids from roller bottles were tested for viral reverse transcriptase activity with $Mg^{++}$ as divalent cation and oligodeoxythymidylate with polyadenylate primer-complex template (oligo dT.poly rA).

Karyotypes were prepared from the Cf2Th-59 and Cf2Th-105 noninfected stationary cultures, the Cf2Th-102 noninfected roller bottle culture, the Cf2Th-100/EIAV-42 (42nd virus passage) stationary cultures and the Cf2Th-96/EIAV-38 roller bottle cultures. Eighteen to 24 h after cultures were passaged, 0.2 μg Colcemid TM (Ciba Pharmaceutical Co., Summit, N.Y.) was added to each of them and then incubated for a further 1, 2, and 4 h. Cultures were then harvested for routine preparation and staining of metaphase chromosomes using 0.05M KCl as the hypotonic solution.

Figure 5:
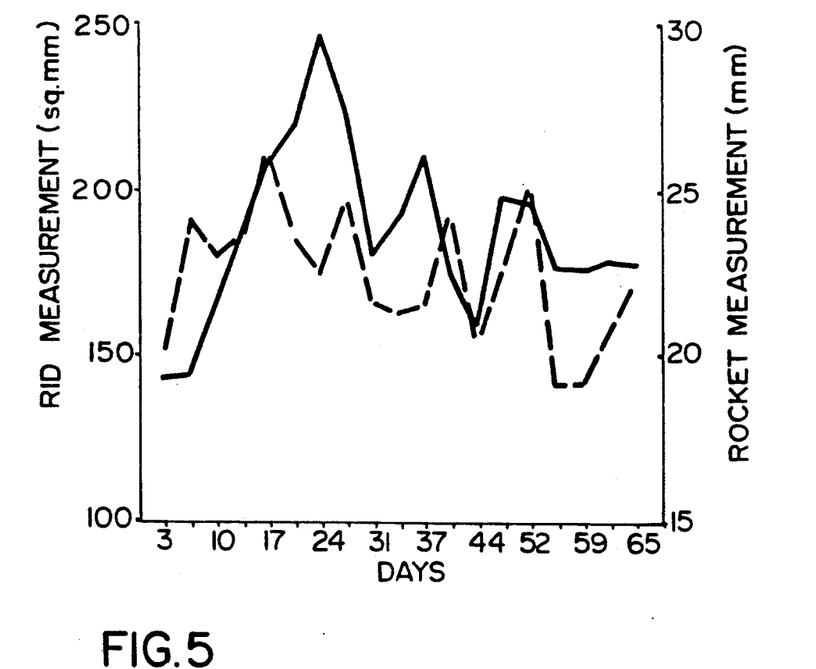
FIG. 5 shows sequential release of ether-extractable EIAV antigen (in vitro) determined by radial immunodiffusion (RID) (solid line) and rocket immunoelectrophoresis (ROCKET) (broken line); and, FIG. 6 shows reverse transcriptase activity during production of EIAV antigens in vitro.

Data from antigen production indicated a correlation between the magnitudes of radial immunodiffusion results and those of the rocket immunoelectrophoresis (FIG. 5). The periodicity of antigen peaks at 6, 17, 27, 41, 52 and 65 days (mean: 12 days) likely represented a viral trait, but did not appear to be related to the frequency of supernatant fluid harvesting and its replacement with fresh medium. Moreover, as the highest percentage of fluorescent cells of the 46th virus passage occurred at 10, 12, 14 and 16 days after trypsinization, the peak of antigen release was likely related to the highest percentage of fluorescent cells. Approximately twice as much antigen was released at the peaks of antigen production than at the low phases of the curve. Sediments recovered from supernatant fluids showed a positive reaction in the immunodiffusion test suggesting that they might also be a good source of EIA antigens.

Figure 6:
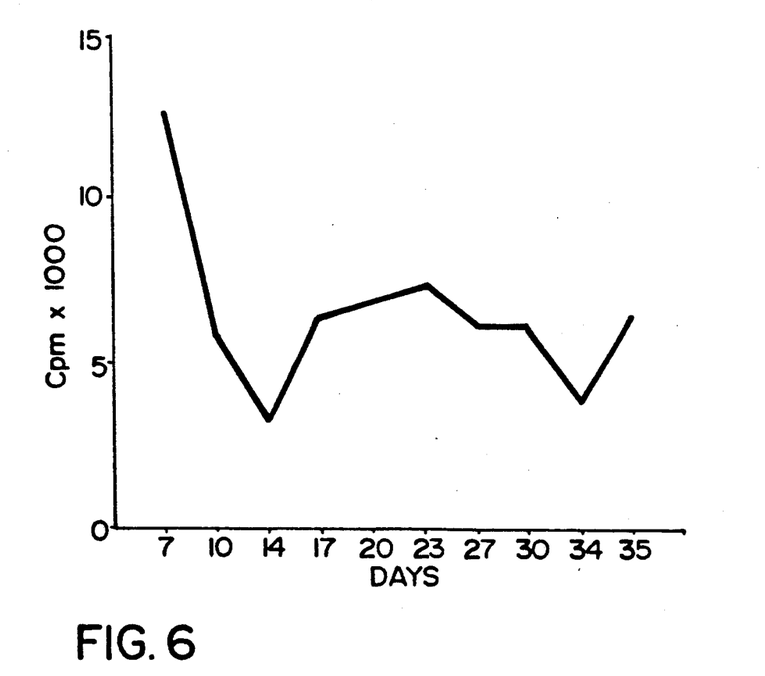

In a parallel study, the viral reverse transcriptase was measured every 3–4 days (starting at day 7 and finishing at day 38). These data are presented in FIG. 6.

EIAV antigens obtained from the Cf2Th/EIA cell line in continuous roller culture appeared comparable to those obtained from EIAV-infected horse spleens and purchased from commercial sources as demonstrated by lines of complete identity in gel diffusion.

At the Cf2Th-59 passage, the modal chromosome number of the uninfected stationary culture was 124 with 14 biarmed chromosomes, including a large submetacentric and large dicentric marker chromosomes, for a modal 138 chromosome arms. This karyotype differed considerably from the karyotype of the Cf2Th-37 passage which had 67 to 75 chromosomes with three to 12 biarmed chromosomes for a total of 70 to 87 chromosome arms and no marker chromosomes.

The Cf2Th-105 and Cf2Th-100/EIAV-42 passages of the noninfected and infected stationary cultures, respectively, had similar karyotypes to each other, namely approximately 112 to 119 chromosomes with approximately 12 biarmed chromosomes for a total number of arms ranging from 124 to 131. Marker chromosomes present were a minute chromosome and a large submetacentric chromosome.

The Cf2Th-102 passage of roller bottle cultures showed two populations of cells; one with approximately 104 chromosomes, the other with approximately 114 to 120 chromosomes. Both populations had approximately 14 biarmed chromosomes. Marker chromosomes present in both populations were a minute chromosome and a large dicentric chromosome. The Cf2Th-96/EIAV-38 of roller bottle cultures had a karyotype resembling one of the cell populations in the Cf2Th-102 passage culture, namely approximately 114 chromosomes with 14 biarmed chromosomes and a minute and a large dicentric marker chromosomes. However, a feature that distinguished the Cf2Th-96/EIAV-38 passage from the Cf2Th-102 passage was the notably increased amount of ploidy in the former.

We have now produced over 350 liters of supernatant EIAV fluids from the Cf2Th/EIAV cell line and concentrated this material to purify the ether-extracted antigen.

Cf2Th EIAV cells have now been maintained for 6 months in roller bottles without subcultivation and have been shown to continuously release EIAV antigens when supernatant fluids were collected twice a week and tested by immunodiffusion, and fresh medium with 10% fetal bovine serum (FBS) was added to the bottles.

These results confirm the permanent infection of the cell line and continuous release of EIAV antigen without subcultivation. In addition, it suggests that the Cf2Th/EIAV cell line could be maintained and grown in suspension culture. Suspension culture can now be considered for large scale suspension in a fermentor.

Precipitin lines not associated with EIAV in immunodiffusion tests were found in some field horse serum specimens with our antigen produced in vitro with 10% FBS, as also observed by others. The main contaminant was found to be bovine serum albumin (BSA) which may be bound non-covalently to EIAV antigens purified by two different techniques described in the original paper.

To eliminate this problem, Cf2Th/EIAV cells were grown in horse serum (HS) and then no non-specific precipitin lines were observed as opposed to EIAV antigens from Pittman Moore. However, as 10 and 5%

HS have been found to be toxic for the cell line, a lower concentration of HS should be used.

Therefore small scale production of EIAV antigens has been performed in roller bottles with 2% HS as follows:

1) Cf2Th/EIAV cells were seeded at high density in 850 cm² roller bottles with medium containing 10% FBS.

2) when the cells were well attached and actively growing on day 2, the cell layer was washed twice with phosphate-buffered saline (PBS) and then fresh medium containing 2% HS was added.

3) cells were maintained in roller bottles for a month although they did not appear to grow as well as in 10% FBS (medium was changed twice a week as described in the original method).

4) it was shown that two washes with PBS removed BSA as follows: fresh medium with 2% HS, harvested 3 days post washing, did not contain BSA as opposed to the two PBS washings which both contained BSA after cell contact.

5) as shown by immunodiffusion, testing of EIAV antigens were continuously released in this 31 day experiment when supernatant fluid was harvested every 3 to 4 days.

The elimination of non-specific precipitin lines (those not associated with EIAV) from the antigen is a major diagnostic advantage that allows diagnosis without several confusing precipitin lines.

Another approach to eliminate FBS consisted of developing a defined medium without FBS. The additional ingredients to be tested have to be assayed: 1) alone, for cell growth promotion and toxicity level, 2) to combine selected ingredients because combination of ingredients may stimulate, synergically or not, cell growth and antigen production, or, alternatively, either have no effect at all or block any activities.

A list of products which preliminary results indicate may be beneficial for promotion of cell growth of the Cf2Th/EIAV cell line is given below:

1) ITS (insulin, transferrin, selenium)+1% HS
   optimum: 10 g/ml
2) Equine albumin, fraction V+1% HS
   optimum: 5 mg/ml
3) FAF (fatty acid free) equine albumin fraction V+1% HS
   optimum: 5 mg/ml
4) linoleic acid+1% HS
   optimum: 2.5 µg/ml
5) TPA (12-o-tetradecanoyl phosphol 13-acetate)+1% HS
   optimum: 10 ng/ml
6) linoleic acid/TPA+1% HS
   optimum: 2.5 µg/1 ng
7) glutamine supplement (e.g. a concentration 4 mM glutamine) appears to be essential to maintain a reasonable cell growth and anchorage for several weeks. This observation may be useful if growth in cell suspension is contemplated and this finding should be recalled if fermentor technology is to be applied.

These preliminary results suggest that 1% HS medium+additive products may permit the development of a medium which will support production of EIAV antigens. However, there is a drawback using HS to produce EIAV antigens in vitro: HS can contain horse viruses other than EIAV which could grow in Cf2Th cells. Of course, it would be ideal if one could develop a serum-free medium permitting high release of EIAV antigens and eliminating potential contamination by serum-products or infectious agents.

Although the specificity of the ether-extracted EIAV antigen from Cf2Th/EIAV cell line has been demonstrated with reference sera and antigens, more evidence had to be demonstrated regarding its relationship with other retroviruses and especially lentiviruses.

Therefore Bovine leukemia virus (BLV) an oncovirus, Bovine syncytial virus (BSV), a spumavirus of unknown pathology and lentiviruses such as Maedi-Visna virus (MVV), caprine arthritis encephalitis virus (CAEV) and bovine Maedi-Visna-like virus (BMVLV) were grown in vitro to prepare antigens. BLV, BSV, MVV, CAEV and EIAV do not cross react in gel diffusion. BMVLV was not tested. Further confirmation was shown when BLV, BSV, BMVLV, MVV and CAEV-specific fluorescent antibodies were applied to cells of the Cf2Th/EIAV cell line. No cross-reaction (specific fluorescence) was observed on the Cf2Th/EIAV cells. In addition, both control Cf2Th and ADRI-Cf2TH/EIAV cells were BVDV-free and IBRV-free.

There is some evidence that another lentivirus could replicate in a tumour cell system. It therefore appears that the concept of using malignantly transformed cell line to produce retroviral antigens and especially lentiviral antigens could be applied to other retroviruses.

Recommended Procedure for Preparation of Cf2Th/EIA Virus Antigens In Vitro

I. Materials

A. Medium and chemicals

1. Trypsin
   EDTA (10×) made in distilled water
   80 ml of H₂O
   10 ml of Dulbecco's Phosphate Buffered Saline (10×) (w/o Calcium & Magnesium)
   10 ml of Trypsin - EDTA
   1 ml of Neomycin Sulfate Solution (10,000 µg/ml)
2. Growth medium (pH 7.4) as per 500 ml of medium
   Dulbecco's Modified Eagle Medium (1×) 500 ml bottle
   25 ml Fetal Bovine Serum (5%)
   1 ml Gentamicin Sulfate (100 µg/ml)
   5 ml anti-PPLO agent (60 µg tylosin/ml)
   0.25 ml Fungizone (0.125 µg/ml)
   5 ml 25 mM Hepes
   1 ml 2N NaOH
3. Fungizone 50 mg/bottle
   Dilute with 20 ml Sterile Distilled Water
4. Hepes
   59.5 gm Hepes diluted in 100 ml of NaOH (prepared as follows: 3.0 gm NaOH in 100 ml Sterile Distilled Water).
5. 2N NaOH
   8 gm NaOH in 92 ml Sterile Distilled Water
6. Source of medium and chemicals

| | | |
|---|---|---|
| 1. | 600-5310 Neomycin Sulfate Solution | GIBCO |
| 2. | 310-4200 Dulbecco's Phosphate Buffered Saline (10×) (without Calcium & Magnesium) | GIBCO |
| 3. | 610-5400 Trypsin-EDTA (10×) | GIBCO |
| 4. | 320-1965 Dulbecco's Modified Eagle's Medium (1×) (4.5 gm glucose/l) | GIBCO |
| 5. | 240-6290 Fetal Bovine Serum | GIBCO |
| 6. | 600-5220 Anti-PPLO Agent (100×) | GIBCO |
| 7. | 845-1344 Hepes (100 gm) | GIBCO |
| 8. | 17-518Z Gentamicin Sulfate 50 mg/ml | M.A. Bioproducts |
| 9. | 43730 Fungizone 50 mg/vial | E. R. Squibb |
| 10. | S-315 Sodium Hydroxide | Fisher Sci. |

B. Glassware and others 1. a. Falcon Tissue Culture Flasks   25 cm²   No. 3013   (100/cs)

| | | | | |
|---|---|---|---|---|
| b. | Falcon Tissue Culture Flasks | 75 cm² | No. 3024 | (500/cs) |
| c. | Falcon Roller Bottle | 1750 cm² | No. 3029 | (15/cs) |
| d. | Falcon Roller Bottle | 850 cm² | No. 3027 | (20/cs) |
| e. | Corning Roller Bottle | 490 cm² | No. 25130 | (40/cs) |
| f. | Corning Centrifuge Tube | 15 ml | No. 25310 | (500/cs) |
| g. | Corning Centrifuge Tube | 50 ml | No. 25330 | (500/cs) |
| h. | Falcon Disposable Pipet | 1 ml | No. 7521 | (1000/cs) |
| i. | Falcon Disposable Pipet | 5 ml | No. 7543 | (200/cs) |
| j. | Falcon Disposable Pipet | 10 ml | No. 7551 | (200/cs) |
| k. | B-D Disposable Syringe | 1 cc with needle | No. 5625 | (100/cs) |
| l. | B-D Disposable Syringe | 20 cc | No. 5661 | (25/cs) |

2. Equipment: RollaCell Tissue Culture apparatus, model RC-42, New Brunswick
3. Addresses

| | | |
|---|---|---|
| 1) | GIBCO | Grand Island, biological Company Grand Island, New York, 14072, U.S.A. |
| 2) | | M.A. Bioproducts Walkersville, Maryland, 21793, U.S.A. |
| 3) | | E. R. Squibb Company Montreal, Quebec, Canada |
| 4) | | Corning tissue Culture Products Fisher Scientific Company |
| 5) | | Falcon Plastic and B.D. Becton, Dickinsons Company Oxnard, California 93030, U.S.A. |
| 6) | | New Brunswick Scientific Edison, N.Y., U.S.A. |

II. Method

All cultures are maintained at 37° C.

A. Stock Cultures

The Trypsin-EDTA and growth media are made as per I.-A. Materials page 20.

1. Control Cells cells are grown in 25 cm² flasks
pour off growth medium
wash monolayer with 3–5 ml of trypsin-EDTA and discard it
add 4 ml of fresh trypsin-EDTA, incubate at 37° C. for 2–3 minutes, collect trypsin-EDTA and cells (pipet 5–8 times) and put in 15 ml centrifuge tube. Add 1 ml of growth medium to stop trypsinization.
spin down in centrifuge at 150 g for 5 minutes
pour off supernatant fluid, split sedimented cells 1:5 ratio, and reseed each 25 cm² flask with a 5 ml mono-dispersed cell suspension
make sure you have a good mono-dispersed cell suspension.

E.I.A.V. Ag. Stock Culture cells are grown in 75 cm² flasks
pour off growth medium (you can keep this for Ag)
wash monolayer with 6 ml of trypsin-EDTA and discard it
add 6 ml of fresh trypsin-EDTA, incubate at 37° C. 2–3 minutes, collect trypsin-EDTA and cells (pipet 5–8 times) and put in 15 ml centrifuge tube. Add 1 ml of fresh medium
spin down in centrifuge at 150 g for 5 minutes
pour off supernatant fluid, split sedimented cells at 1:5 ratio, and reseed each 75 cm² flask with a 20 ml mono-disperse cell suspension.

N.B. The control cells and EIA-infected cell stock are subcultured twice a week (Monday and Friday) at 1:5 split ratio.

B. Antigen Production with Medium Supplemented with FBS

The E.I.A. Ag for production has been tried in three (3) sizes of roller bottles.
1. 490 cm² Corning
2. 850 cm² Falcon
3. 1750 cm² Falcon No major differences were seen in the roller bottles used, as per the growth of cells.

Take a 75 cm² flask ($1 \times 10^7$ cells/flask) and trypsinize as per the method used in Stock Cultures (see II.-A.-2. Methods page 23).

2. a. If you are using a 490 cm² bottle, seed cells with 100 ml D-MEM, supplemented with 10% FBS to obtain an adequate buffering of medium.
  b. After the 1st collection of supernatant fluid, replace it with 50 ml of fresh medium (D-MEM, 5% FBS) for each successive harvest.
3. a. If you are using a 850 cm² bottle, seed cells into 150 ml medium (D-MEM, 10% FBS).
  b. Replace by 100 ml of medium (D-MEM, 5% FBS).
4. a. If you are using a 1750 cm² bottle add the cells into 300 ml of medium (D-MEM, 10% FBS).
  b. Replace by 150 ml of medium (D-MEM, 5% FBS).
Revolution per minute = 0.2 rpm (RC-42 RollaCell ™ New Brunswick Scientific Co., Edison, N.J.)

N.B. The harvested supernatant fluid is stored at −20° C. until further processing.

III. Notes

A. We started by using 1×75 cm² flask of cells into one roller bottle; the size of roller bottle being used did not matter (490 cm², 850 cm² or 1750 cm²).

B. Sometimes a ratio of 1:2, 1:3 or 1:4 (75 cm² flask roller/bottle) was used. The cells were usually 90 to 100% confluent within 48 hours.

C. The supernatant fluids were harvested every 3 and 4 days (Monday and Friday).

D. The roller bottles were replaced with new ones between 28 and 35 days. Once the roller bottles are set up, check them periodically for cell growth and absence of extraneous contaminants. At approximately 24 days the cells start to detach; you will then have to decide when to set up the new roller bottles.

E. The new roller bottles are always set up from the stock cultures in 75 cm² flasks. The old ones are just discarded.

F. The stock cultures are always passed on the Monday and Friday, continuously, as follows:
1. 3×25 cm² flasks of control cells at one time
2. 5×75 cm² flasks of E.I.A. Ag. at one time.

N.B. If you have to set up a large number of roller bottles at one time, you must build up the stock cultures first.

G. In order to obtain the best buffering capability of the medium, 100 ml, 150 ml, or 300 ml of medium were used for seeding of the cells.

IV. Quality Control

A. Fetal Bovine Serum

The FBS is checked for the following antibodies:
1. BLV: Bovine Leukemia Virus
2. BSV: Bovine Syncytial Virus
3. E.I.A.: Equine Infectious Anemia (to check for cross-contamination)
4. M.V.: Maedi-Visna Virus (to check for cross-contamination)
5. BMVLV: Bovine Maedi-Visna-like virus
6. IBR: Infectious Bovine Rhinotracheitis
7. BVD: Bovine Virus Diarrhea
8. PI$_3$: Para Influenza III The following are checked by GIBCO supplier:
Bacterial and fungal sterility
Mycoplasma sterility
Toxicity and capability to stimulate the growth of cells.

B. Equine Infectious Anemia Antigen

1. Samples of the bulk AG are tested each week by immunodiffusion.
2. The Cf2Th/EIA is checked every 10th passage by immunofluorescence.
3. The Cf2Th/EIA tissue culture is examined from time to time by electron microscopy.
4. Samples are checked for Mycoplasma.
5. Samples are checked for bacterial contaminants and fungi.

Antigen Production With Medium Supplemented With Horse Serum HS

1. Follow steps 1–4 under the heading "B. Antigen Production" above.
2. Collect the supernatant fluid 2–3 days after seeding cells. Note at this stage the medium is supplemented with FBS.
3. Wash cells twice with 100 ml PBSF/wash for 30 minutes in RollaCell.
4. Add D-MEM in which FBS has been substituted by 2.0% HS.
5. Harvest supernatant fluid every 3–4 days and replace by fresh D-MEM supplemented with 2% horse serum. Store supernatant fluid at −20° C. until processed further.

Minimally, HS is checked for antibodies to EIAV and equine herpesvirus I (rhinopneumonitis), but there are other equine viruses for which HS could be checked.

Quality control of sera is a tedious and long process, nevertheless a very important one in the production of antigens. It is the responsibility of the antigen producer to decide to what extent he wants to pursue the quality control of sera which may involve not only detection of antibodies but also attempts to isolate viruses. The above list of viruses is not exhaustive.

Trypsin and trysin-EDTA are sometimes contaminated by porcine parvovirus. Testing of Cf2Th/EIAV and Cf2Th control cell lines by immunofluorescence for the presence of porcine parvovirus after such cell lines had been inoculated by porcine parvovirus showed that such cell lines do not support the replication of porcine parvovirus. Therefore trypsin and trypsin-EDTA can both be used without inconvenience to trypinize Cf2Th/EIAV and Cf2Th/BMVLV cell lines.

Monitoring Antigen Production

1. Examine roller bottles under a phase-contrast microscope (twice a week) for the presence of contaminants (bacteria, yeast, fungi) and for cell growth.
2. Test a sample of the bulk antigen each week by immunodiffusion.
3. Every other week, take 5 ml supernatant fluid and test for isolation of bacteria, yeast, fungi and mycoplasma (using aerobic, anaerobic, Sabouraud and specific mycoplasma media).
4. The Cf2Th/EIAV cell line is checked every 10th subculture for EIAV by immunofluorescence and, from time to time, by electron microscopy.

Concentration of Antigen by Pellicon Cassette Ultrafiltration System

1. Freeze and thaw supernatant fluid five (5) times.
2. Centrifuge at 1000 g for 20 minutes (keep sediments for further extraction of antigens).
3. Pool supernatant fluids in a four-liter beaker.
4. Concentrate supernatant fluids in the Pellicon cassette system.
5. Add more supernatant fluid to the beaker as the material is concentrating down.
6. Concentrate the supernatant fluid in batches of 10 liters until 250 to 300 ml of concentrated antigen per batch is obtained.
7. Freeze concentrated antigens at −20° C. until antigen purification performed.
8. Flush the Pellicon cassette system with two (2) liters 1×PBSF.
9. Start the next batch.
10. Each 10 liter batch takes about 2 hours to concentrate.
11. Wash the Pellicon cassette system with two (2) liters of 1×PBSF. Then fill cassette with NaOH (0.1M) from ½ hour to 24 hours to clean the filter. Flush with five (5) liters or more distilled water until all NaOH is removed from the filter (no colour left). Fill Pellicon cassette system with 1.0% formalin and remove the filter. Then, store the filter in sealed container filled with 1.0% formalin.
12. Check tubing carefully since the peristaltic pump can damage the tubes (after each use, move tubes up 6 inches).

Note: The filter may sometimes become blocked because the concentrated supernatant fluid becomes too viscous, in which case, reverse the flow to unblock the filter.

The specificity of Cf2Th/EIAV antigens has been demonstrated by testing for cross-reactivity with five other retroviruses from large domestic animals: BLV, BSV, MVV, CAEV and BMVLV. In the case of BMVLV (a lentivirus), specific fluorescent antibodies did not react with EIAV antigens when BMVLV antiserum was applied on cells of the Cf2Th/EIAV cell line in an indirect immunofluoroescence test. Conversely, BMVLV infected cells did not cross-react with antibodies specific to EIAV.

Discussion of Rationale

The ADRI-Cf2Th/EIAV cell line is currently used for antigen production from the 30th subculture onward because EIAV permanent infection appeared to be well established as shown by the continuous release of antigen in the supernatant fluid. Cf2Th/EIAV cells were seeded in D-MEM supplemented with 10% FBS for rapid attachment and growth at high density. Medium was changed 2-3 days after seeding. Supernatant fluid containing antigens was harvested every 3 to 4 days (Monday and Friday) for convenience, but a 2 to 3 day schedule of harvesting may be more appropriate to prevent the medium from becoming too acidic and to remove antigen-rich detached and dead cells, because enzymes and other toxic products released from the dead cells might damage the live cells. At 25 to 35 days after seeding, a new set of roller bottles was prepared because the number of cells and amount of debris had increased in the supernatant fluid to levels at which the rate of antigen production could be affected, although cells continued growing as observed by the presence of mitosis. However, the continuous release of the antigen was observed when the Cf2Th/EIAV cells were maintained without trypsinization for 6 months in D-MEM supplemented with 10.0% FBS and harvested on a 3-4-day schedule. Maintenance of high cell density was more difficult in D-MEM supplemented with 2.0% HS after a month of culture possibly because the lack of nutrients and/or the low concentration of HS did not meet all the growth and maintenance requirements of the Cf2Th/EIAV cell line (the particular HS used was toxic to the Cf2Th/EIAV cells at 5.0 and 10.0% concentration in D-MEM).

Release of EIAV antigens into the supernatant fluid was continuous, but fluctuated with a periodicity of 12 days (mean) on antigen peaks. Although cells were not counted in roller bottles, it is possible that the fluctuation of antigen release into the supernatant fluid was related to the cell density, since changes of cell density were observed by phase contrast microscopy and periodic fluctuations of cell release were seen in the harvested supernatant fluid. Other work has shown that the number of virions released into the supernatant fluid from EIAV-infected fibroblasts was proportional to the number of cells, but was not related to the growth phase of the culture. Then, it is possible that peaks of antigen release occurred when Cf2Th/EIAV cells, both attached on the plastic wall and free in the supernatant fluid, were at the highest cell density.

Quality control and the cost of antigen production are other important factors in manufacturing antigens. Quality control first involves monitoring of extraneous contaminents as discussed above. Secondly, it involves the potential permissivity of the Cf2Th cell line to viruses other than EIAV, for example, infectious bovine rhinotracheitis virus (IBRV) has been observed to replicate in the Cf2Th cell line. Sera used in the production of antigen must be tested for all viruses which may replicate in cell line being used for antigen production. Thirdly, the cost of a unit of antigen is a limiting factor in diagnosis. If antibiotics could be eliminated from medium when proper aseptic techniques are applied, it would be cheaper and it would also be beneficial for cell production since continuous contact of cultured cells with antibiotics may have an undesirable effect on cell lines. Moreover, if the percentage of FBS can be lowered from 10 to 5%, it will reduce the cost of complete medium, since serum accounts for 50 to 60% of the total price of medium. Finally, purification of antigen was also facilitated when extraneous proteins were kept to a minimum, thereby reflecting on the quality of antigens and reducing the cost of antigen production on the total overhead from the production of antigen.

Growth of the Cf2Th/EIAV Cell Line in Suspension Culture and in Serum-Free Medium Cf2Th/EIAV cell lines can be grown in suspension culture without microcarriers either in FBS or HS plus additives. They release antigens when maintained in such sera. Preliminary experiments indicate that the Cf2Th/EIAV cell line can grow in serum-free medium and release EIAV antigens into supernatant fluid. The Cf2Th/EIAV cell line has been continuously grown in suspension culture both in 10% FBS and serum-free media for 42 days. The cells were not removed from the stirrer flasks and the medium was changed every 3-4 days as in roller bottles. A 9-day periodicity of cell growth peak was observed in suspension culture.

The serum-free medium used in the above experiments is given below.

Composition of the experimental serum-free medium used in MCS Techne™ stirrer glass flask (cf2Th/EIAV cell line):

| | Ingredient | Concentration | Cat. No. | Company | Remarks |
|---|---|---|---|---|---|
| 1 | Dulbecco-MEM (D-MEM) | 4.5 gm/glucose/liter | 320-1965 | GIBCO | |
| 2 | Hepes | 25 mM | 845-1344 | GIBCO | |
| 3 | NaOH | 2N | AC 8370 | Anachemia | to adjust final pH at 7.4–7.5 |
| 4 | Neomycin | 100 µg/ml | 600-5310 | GIBCO | |
| 5 | $CaCl_2$ | 1 mM | 20,294-4 | Aldrich | DMEM already contains 2 mM, then total: 3 mM |
| 6 | Albumin, horse | 2.0 to 2.5 mg/ml | A-9888 | Sigma | concentration has to be finalized |
| 7 | ITS mixed (insulin, transferrin, selenium) | 20 µg/ml | 40350 | Collaborative Research | concentration has to be finalized |
| 8 | TPA (Phorbol 12-myristate 13-acetate) | 10 mg/ml | P-8139 | Sigma | concentration has to be finalized |
| 9 | Linoleic acid | 10 µg/ml | 4364 | Calbiochem (Behring diagnostic - Hoechst) | concentration has to be finalized |
| 10 | Glutamine | 4 mM | | | 4 mM is already in the DMEM. 8, 12, 18 mM |

| Ingredient | Concentration | Cat. No. | Company | Remarks |
|---|---|---|---|---|
| | | | | glutamin appear to block Ag release to some extent - thus concentration of glutamin has to be finalised. |

N.B.
1) 6, 7, 8, 10 was determined in DMEM + 1.0% HS and checked separately; now we need to "finalise" the optimum concentration in regard to the particular medium above
2) R.P.M. 35 to 40; probably too fast; prolonged culture may clump lightly.

As described below BMVLV has been shown to replicate in the Cf2Th cell line as demonstrated by syncytium induction, immunofluorescence and electron microscopy (BMVLV). These results suggest that the Cf2Th cell line, infected with such a virus provides a potential cell system to produce viral antigens in vitro. BMVLV produces syncytia so that detailed methodology for large-scale production of antigens may differ somewhat from that used in the production of EIAV antigens.

Production of Bovine Maedi Visna-like Virus (BMVLV) antigens

BMVLV in Cf2Th cells has been serially subcultured more than 90 times. The Cf2Th/BMVLV cell line has been shown to release BMVLV antigens continuously using indirect immunofluorescence, electron microscopy, syncytium induction (10 to 40 nuclei) and virus titration. A titre of $1\times10^{-8}$/0.1 ml was found in the 28th virus passage in plastic flasks and of $1\times10^{-10}$/0.1 ml in the 43rd virus passage at 7 days in suspension culture.

The Cf2Th/BMVLV cell line grows and releases antigens in suspension culture maintained in 10% FBS fetal bovine spleen for 7 days.

1. Cell and Virus

Cultures of control bovine fallopian tube (BFT) cells and BFT cells infected by BMVLV (BFT/BMVLV) were graciously provided by Dr. M. J. Van Der Maaten (U.S. Department of Agriculture, National Animal Disease Center, Ames, Iowa, U.S.A.). FBS, fetal bovine cornea (FBCor), fetal bovine choroid plexus (FBCP), fetal lamb spleen (FLS), fetal lamb cornea (FLCor), and fetal lamb choroid plexus (FLCP) cells were prepared by the explant technique of Bouillant et al, Ann. Rech. Vet. (1981), 12, 385-395. All cells above were grown in complete Dulbecco minimum essential medium (DMEM, 4.5 g/l glucose) supplemented with 10% fetal bovine serum (FBS), 25 mM Hepes and 100 μg neomycin. The pH was adjusted to 7.4 with 2N sodium hydroxide solution.

BFT/BMVLV cells were both serially cocultured with BFT or BFS cells and serially passed without addition of fresh BFT cells. Two approaches were followed to infect different cells types by BMVLV (Table 2). Firstly, infected supernatant fluids from BFT/BMVLV cells were harvested when 50% or more of the cultures showed large syncytia and cell necrosis and filtered on 22 μm filter unit (Millex-HA TM). Cells to be tested for virus replication were treated for 30-40 minutes at 37° C. with 25 mg/ml DEAE-Dextran TM, then washed once and 1-2 ml of BMVLV supernatant fluid were absorbed for 4 hours on the cell layer. Complete DMEM was added at the end of the absorption period. Secondly, BMVLV infected cells (Table 2) were cocultured with the above six diploid lines and serially subcultured. Moreover, two established cell lines were also tested as above for BMVLV permissiveness namely the Cf2Th line from canine thymus ATCC CRL 1430 and the mpf line from ferret brain ATCC CRL 1656.

Bovine cell lines were free of bovine leukemia, bovine syncytial, infectious bovine rhrinotracheitis, bovine virus diarrhea and BMVL viruses as shown by immunofluorescence. Ovine cells were free of Maedi-Visna caprine-encephalitis-arthritis, bovine leukemia virus, bovine diarrhea virus and BMVLV by immunofluroescence. Mpf and Cf2Th cell lines were free of EIAV and all the viruses listed above.

2. Virus titration

BMVLV was titrated either on FBS or Cf2Th cells as described above for EIAV. The end point was calculated as the virus highest dilution of infected cells in which syncytia and immunofluorescence were observed.

3. Indirect immunofluorescence

BMVLV-infected cell cultures and uninfected cell cultures were flooded with a pre-determined dilution of control (BMVLV) positive and negative sera and incubated for 30 minutes at 37° C. The slides were washed with phosphate buffered saline (PBS). They were then overlayed with antispecies-antibody conjugated with fluorescence isothiocyanate and incubated for 30 minutes at 37° C. The slides were then washed in PBS followed by distilled water, air-dried, mounted in 10% glycerol-PBS solution and examined by epi-illumination with a fluorescence microscope.

4. Electron microscopy

Briefly, cells were washed once with phosphate, fixed for 1 hour at room temperature in 2.5% glutaraldehyde, then rinsed again and post-fixed for 1 hour at room temperature in 2% osmium tetroxide and processed as previously described, in Bouillant et al J. Nat. Cancer Inst. (1984) 72, 1075-1084.

5. Antisera

Pre-inoculation (no. 6397 and 6438) and post-inoculation (no. 6397, 6438 and 6552) sera were kindly provided by Dr. Van Der Maaten, NADL, USDA, Ames, Iowa, USA.

6. Immunodiffusion tests

Supernatant fluid from FBCor/BMVLV and Cf2Th/BMVLV subcultures were pelleted at 60.000 g/1 hour. Pellets were suspended in PBS and a portion was precipitated with polyethylene glycol (MW 6,000 Daltons) as described for EIAV antigen by Malinquist et al, Arch. Gesante Virusforsch. 42, 361 (1973). A second portion was precipitated with ammonium sulphate. In both cases, precipitates were solubilized in and dialysed against PBS. Following dialysis, an amount of each preparation was treated with an equal volume of anhydrous ether which was allowed to evaporate. The ether treated and untreated preparations were used as antigens in gel diffusion studies using the antisera described above. The medium for gel diffusion consisted of 1% Noble agar melted in 0.1M tris HCl, pH 7.2, containing 1.0 M NaCl and 1.0 mM EDTA. Various dilutions of all reagents were tested.

7. Suspension culture

Cells were grown in suspension cultures without micro-carriers in Techne TM 500 ml culture vessels with 200 ml DMEM medium as described above for cell growth in stationary culture. Cells were counted every 2-3 days, and medium changes as described in results.

8. Mycoplasma testing

Cells were grown on slides, fixed directly with Carnoy's fixative, air dried, stained with DNA-specific fluorescent Hoechst 33258 TM and examined microscopically. Diploid cells Table 2 shows the permissiveness of six cell lines (diploid and aneuploid) in addition to the two cell lines (BFT/BMVLV and FBS/BMVLV) graciously given by Dr. Van Der Maaten. Moreover, it provides the methodology used to determined the latent viral infection in vitro and the rescue of BMVLV on Cf2Th cells. All eigth cell lines became infected after inoculation with BMVLV. All underwent a latent infection with the exception of both FBCor and Cf2Th/BMVLV cell lines. The BFT/BMVLV cell line was cocultured and subcultured a few times, but appeared to generate latent infection since cocultivation was necessary to induce syncytium induction and transfer BMVLV infection to other cell types.

These results show that latency indicates that a cell is permanently infected by BMVLV, but evidence of viral infection without virus rescue in permissive and virus-productive cells is lacking such as shown by absence of three criteria of BMVLV infection: syncytium induction (<10 nuclei), positive immunofluorescence to BMVLV and expression of a typical lentivirus morphology at the electron microscope.

FBS cells cocultured with BFT/BMVLV cells developed large syncytia (30 nuclei). Syncytia were rarely observed in serial FBS/BMVLV subcultures to which no fresh FBS cells were added. At the 4th, 5th, 6th, 7th, 12th, and 21st serial subcultures, fractions of these respective cultures were cocultured with fresh FBS cells. Then syncytia were observed, thus indicating BMVLV expression. Also positive immunofluorescence to BMVLV, observed in the 21st serial culture cocultured with FBS cells, confirmed the BMVLV infection of the FBS/BMVLV cells. BMVLV infection of FBS/BMVLV cells were further confirmed after cocultivation of the 21st serial FBS/BMVLV subculture with Cf2Th cells since the three above criteria of infection were demonstrated in these cocultures. These criteria of infection could not be demonstrated, when the 12th and following serial FBS/BMVLV subcultures were examined for presence of BMVLV, thereby indicating that absence of syncytium induction and positive immunofluorescence to BMVLV was corrolated with the absence of virus expression at the electron microscope. Towards the 10-12th serial subcultures, FBS/BMVLV cells became more refractive, confirming the suggestion that FBS/BMVLV cells may be established in a continuous cell line.

When FBCP cells were cocultured with the 4th FBS/BMVLV subculture expressing syncytia (fresh FBS cells were added), syncytia were observed in the two subsequent serial FBCP/BMVLV subcultures, but disappeared after further serial subcultures. A few syncytia were observed when the 21st serial FBCP/BMVLV subculture was cocultured with FBS cells. The 22nd serial FBCP/BMVLV was cocultured with Cf2Th cells and then the three criteria of BMVLV infection were demonstrated in the cocultures, confirming that FBCP cells, inoculated by BMVLV, carried BMVLV in a silent form.

FBCor cells were cocultured with the 12th FBS/BMVLV subculture expressing syncytia. Few syncytia developed in the 1st FBCor/BMVLV subculture and numerous ones were observed in each of the 17 subsequent serial cultures to which fresh FBCor cells were added. As over 60% of the cell layer showed both syncytia (30 nuclei) and cell necrosis 4-7 days after addition of fresh FBCor cells, refeeding of fresh cells was required for virus replication. The FBCor/BMVLV cells filled the three criteria of virus infection (syncytia, immunofluorescence and lentivirus morphology). Cell-free supernatant fluid of both the 11th and 13th serial FBCor/BMVLV subcultures had a titer of $1 \times 10^5/0.1$ ml. The above three criteria of infection were also demonstrated when cells of the 13th FBCor/BMVLV cells were cocultured with Cf2Th cells.

FLS and FLCor cells were separately cocultured with the 10th FBS/BMVLV subculture expressing syncytia. Few syncytia were observed in both sets of cocultures and in the two-three subsequent serial subcultures, but no evidence of syncytia, positive immunofluorescence to BMVLV and lentivirus morphology occurred at the 4th serial subculture and thereafter. When the 9th serial FLS/BMVLV and the 6th serial FLCor/BMVLV subcultures were cocultured with Cf2Th cells, the three criteria of BMVLV infection were demonstrated, thus indicating that both ovine cell lines carried BMVLV in silent form.

All above diploid, control and BMVLV-infected cells were subcultured to a 1:2 ratio.

Mpf cells were cocultured, with the 12th FBS/BMVLV subculture expressing syncytia, at a 1:2 ratio until the 6th serial subculture, followed by 1:4 until the 10th serial subculture and 1:5 thereafter. Cells of the 8th serial mpf/BMVLV subculture were cocultured with fresh FBS cells and few syncytia were observed in the subculture next to cocultivation. Cells of the 11th serial mpf/BMVLV sulculture were cocultured with fresh Cf2Th cells and the three criteria of BMVLV infection were demonstrated. When the 19th serial mpf/BMVLV subculture was subcultured at a 1:10 ratio, a few large syncytia (10 nuclei) were observed. These syncytia were similar to syncytia induced in diploid cells by BMVLV, but different from naturally occurring syncytia (5-10 nuclei) in the mpf cell line. Criteria of BMVLV infection could not be demonstrated in the serial mpf/BMVLV subcultures, although they were infected such as shown by cocultivation with Cf2Th cells and demonstration of the three criteria of BMVLV infection.

Cf2Th cells of the 82nd subculture were inoculated with 2 ml of cell-free BMVLV suspension from the supernatant fluid of the 12th FBCor/BMVLV subculture, sampled 6 days after trypsinization. Large syncytia were observed in the third serial subculture and continuously thereafter. Syncytia had a similar grouping and arrangement than those observed in BMVLV-infected FBCor cells and contained from 30 to 50 nuclei. They differed by their number and arrangement from those routinely encountered in non-infected Cf2Th cells, the syncytia of which contain from 5 to 10 nuclei. The Cf2Th/BMVLV cell line was subcultured at a 1:2 ratio in the first five subcultures and 1:3 thereafter. When the first 20 serial subcultures were subcultured at a 1:5 ratio, there was too much cell destruction to carry on subsequent subcultures without adding fresh Cf2Th cells. The rapid population doubling of Cf2Th cells appeared to compensate cell death caused by BMVLV when cells were subcultured at a 1:3 ratio. Occurrence of cell death was less dramatic after the 20 serial subculture and a permanently BMVLV-infected ADRI-Cf2Th/BMVLV cell line was established by subculturing cells twice a week at the 1:3 ratio. Although the cell line is maintained at the 1:3 ratio, it appears that the 1:5 ratio could be maintained for at least 10 serial subcultures without dramatic loss of cells after the 50th serial subculture and onwards. The three criteria of BMVLV infection were observed during the 80 serial subcultures of the ADRI-Cf2Th/BMVLV cell line (Table 3).

Figure 7:
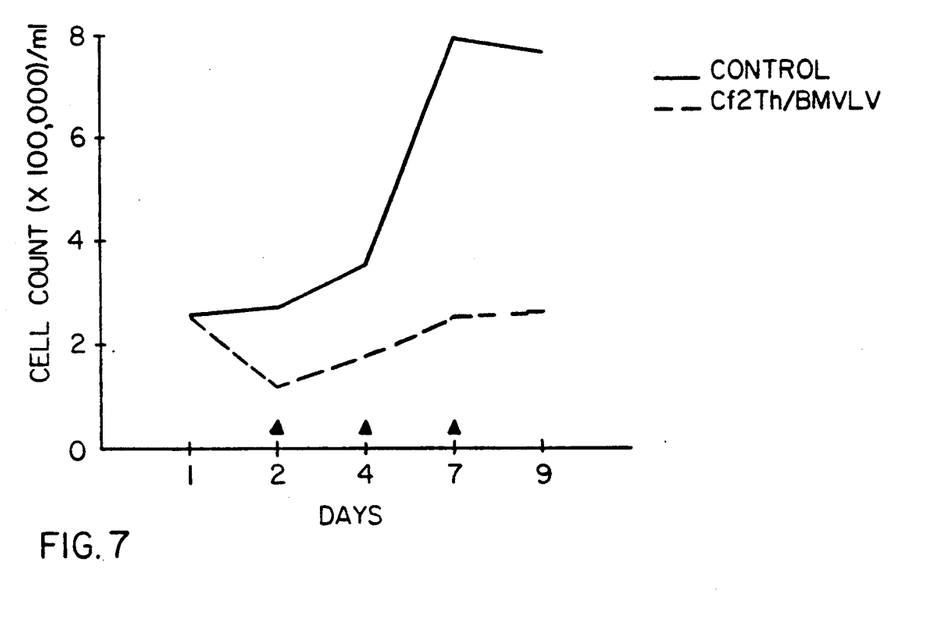
FIG. 7 shows comparative cell growth of non-infected control Cf2Th-124 and ADRI-Cf2Th-126/BMVLV-44 subcultures in suspension culture. The arrow indicates a change of medium.

Non-infected control Cf2Th cells and ADRI-Cf2Th/BMVLV cells were grown in suspension culture. Results of comparative growth kinetics indicated that growth rate of the former was 2 to 3 times higher than that of the latter (see FIG. 7). A titre of $1 \times 10^{10}/0.1$ ml (the highest dilution tested) was shown when the supernatant fluid from the 43rd serial subculture of Cf2Th/BMVLV cell line, sampled 7 days after seeding the flask, was tested in the Cf2Th cells by demonstration of syncytium induction and positive indirect immunofluorescence to BMVLV.

The ADRI/Cf2Th/BMVLV is BVDV free and did not show any detectable cross-reactivity with EIAV such as shown by immunofluorescence.

Perinuclear and cytoplasmic BMVLV antigens were observed by immunofluoresence. Pre and post sera, kindly supplied by Dr. M. J. Van Der Maaten, were negative and positive to BMVLV respectively when tested on BMVLV-infected cells by indirect immunofluorescence. Concentrated BMVLV antigens, either non or ether-extracted, were not precipitated by BMVLV antisera in immunodiffusion tests.

Budding viruses on the plasma membrane and mature viruses with conical to tubular cores in the extracellular space were observed in all cell systems infected with BMVLV which induced BMVLV syncytia. Firstly, virions were found at different periods of time after seeding cells from various cell lines (Table 4). Secondly, examination with the electron microscope was greatly facilitated when areas rich in syncytia were located on fixed monolayers, sampled and processed for electron microscopy. Most syncytial areas contained enough viruses with a typical morphology of lentiviruses.

A cell line producing EIAV antigens is being maintained at the Animal Diseases Research Institute, Agriculture Canada, Nepean, Canada K2H 8P9 and is coded as ADRI-Cf2ThX$_1$/EIAVY$_1$ where X$_1$ denotes the number of cell passages and is an integer of at least 25 and Y$_2$ denotes the number of virus passages and is an integer of at least 1.

A cell line producing BMVLV antigens is being maintained at the Animal Diseases Research Institute, Agriculture Canada, Nepean, Canada K2H 8P9 and is coded as ADRI-Cf2ThX$_2$/BMVLVY$_2$ where X$_2$ denotes the number of cell passages and is an integer of at least 25 and Y$_2$ denotes the number of virus passages and is an integer of at least 1.

Cell line nomenclature operates as follows. ADRI-Cf2Th 59/EIAV 1 means that the cell line has been passaged 59 times, and the virus has been passaged once. Subsequent passaging of this cell line (with virus) could lead, for example, to ADRI-Cf2Th 259/EIAV 201 after an additional 200 passages. This nomenclative allows the user immediately to identify at what passage number the cell line was treated with virus and allows appropriate controls to be kept for, for example, karyotype analysis.

TABLE 2

BMVLV permissiveness of cell lines: detection of latent and productive infections in serial BMVLV subcultures.
BMVLV was rescued from latently infected subcultures by cocultures with BMVLV-permissive Cf2Th cells

| Denomination of BMVLV-infected cell lines | CELL Type | CELL Species | CELL Tissue (A) | BMVLV-Free cells cocultured with BMVLV-infected cells (B) | BMVLV-infected cell lines (A & B) cocultured With virus-free cells | BMVLV-infected cell lines (A & B) cocultured Syncytium[a] induction | Serial BMVLV subcultures w/o cocultures No. of subcultures | Serial BMVLV subcultures w/o cocultures Syncytium induction and immuno-fluorescence[b] | Virions (EM)[c] |
|---|---|---|---|---|---|---|---|---|---|
| BFT/BMVLV | diploid | bovine | Fallopian tube (BFT) | BFT/BMVLV | BFT | +[d] | n.d.[d] | n.d. | n.d. |
| FBS/BMVLV | " | " | Spleen (FBS) | " | FBS | + | 27 | −[d] | − |
| FBCor/BMVLV | " | " | cornea (FBCor) | FBS/BMVLV | FBCor | + | 20 | + | + |
| FBCP/BMVLV | " | " | choroid plexus (FBCP) | " | FBS | + | 22 | − | − |
| FLS/BMVLV | " | ovine | spleen (FLS) | " | n.d. | n.a. | 17 | − | − |
| FLCor/BMVLV | " | " | cornea (FLCor) | " | n.d. | n.a. | 9 | − | n.d. |
| Cf2Th/BMVLV | aneuploid | canine | thymus (Cf2Th) | FBCor/BMVLV supernatant fluid | Cf2Th | + | 80 | + | + |
| Mpf/BMVLV | aneuploid | ferret | brain (mpf) | FBS/BMVLV | FBS | + | 31 | − | − |

| Denomination of BMVLV-infected cell lines | BMVLV Rescue by Cf2Th cocultures Syncytium induction and immunofluorescence | BMVLV Rescue by Cf2Th cocultures Virions (EM) | Latency in serial BMVLV subcultures | Remarks |
|---|---|---|---|---|
| BFT/BMVLV | n.d. | n.d. | n.a. | Van Der Maaten cell line |
| FBS/BMVLV | + | + | + | Ref. 1 |

TABLE 2-continued

BMVLV permissiveness of cell lines: detection of latent and productive infections in serial BMVLV subcultures.
BMVLV was rescued from latently infected subcultures by cocultures with BMVLV-permissive Cf2Th cells

| | | | | |
|---|---|---|---|---|
| FBCor/BMVLV | + | + | − | Virus-productive infection and cell lysis |
| FBCP/BMVLV | + | + | + | |
| FLS/BMVLV | + | + | + | |
| FLCor/BMVLV | + | + | + | |
| Cf2Th/BMVLV | n.a. | n.a. | − | Virus productive infection continuous production of antigen |
| Mpf/BMVLV | + | + | + | |

[a] Syncytium induction by BMVLV
[b] Indirect immunofluorescence to BMVLV antigens
[c] EM: electron microscopy
[d] + or −: positive or negative reaction; n.d.: not done; n.a.: not applied

TABLE 3

Evidence of the permanent BMVLV infection in the Cf2Th/BMVLV cell line demonstrated by three criteria: syncytium induction, electron microscopy and indirect immunofluorescence.

| Virus passage | Syncytium induction | Electron miroscopy | Immuno fluorescence | Virus Titer R (0.1 ml) | Remarks |
|---|---|---|---|---|---|
| 1-10 | +[a] | +(9)[b] | nd | nd | |
| 11-20 | + | +(17) | +(18,19) | $10^{6(14)}$ | six days supernatant fluid |
| 21-30 | + | nd (a) | +(21) | $10^{8(28)}5$ | four days supernatant fluid |
| 31-40 | + | nd | +(38) | nd | |
| 41-50 | + | +(41) | +(42) | $10^{10(43)}$ | titrated from suspension culture 7 days after cell seeding |
| 51-60 | + | nd | +(51) | nd | |
| 61-70 | + | +(61) | +(68) | nd | |
| 71-80 | + | +(78) | +(77) | nd | |
| 81-90 | + | +(86) | +(82) | nd | |

[a] +: positive reaction; n.d.: not done
[b] subculture number

TABLE 4

Sequential detection of viruses in cell lines during a 96 h period of time

| CELL LINES: | HOURS | | | | | | REMARKS |
|---|---|---|---|---|---|---|---|
| | 3 | 7 | 24 | 48 | 72 | 96 | |
| Cf2Th/BMVLV-68 | nd[a] | − | − | − | + | − | Serial subculture: 68 |
| CF2Th/FBCP/BMVLV-17 | nd | + | − | + | + | − | BMVLV-infected diploid cell line |
| CF2Th/FBCor/BMVLV-27 | nd | − | − | − | − | + | cocultured with Cf2Th cells. |
| CF2Th/FLS/BMVLV-26 | − | − | + | − | − | − | Number refers to serial subculture after cocultivation with Cf2Th cells. |

[a]: nd: not done; − or +: absence or presence of virions (in 5 to 10% of the examined electron microscopic field).

The Cf2Th/BMVLV cell line has been deposited with the American Type Culture Collection with the ATCC accession number CRL 10816. BMVLV is now conventionally known as Bovine Immunodeficiency Virus (BIV).

The embodiments of the invention in which an exclusive property or privilege is claimed are defined as follows:

1. A transformed canine Cf2Th thymus cell line infected with bovine Maedi-Visna-like virus, the cells of which cell line have continuously reproduced themselves for at least 25 passages after initial infection with said virus, and continuously produce viral antigens.

2. A transformed cell line according to claim 1, comprising a canine thymus cell line Cf2Th (ATCC CRL 1430) infected with bovine Maedi-Visna-like virus, the cells of which cell line have continuously reproduced themselves for at least 25 passages and continuously produce viral antigen, said cell line carrying the designation $Cf2ThX_2/BMVLVY_2$ wherein $X_2$ denotes the number of cell passages and is an integer of at least 25 and $Y_2$ denotes the number of virus passages and is an integer of at least 1.

3. A method of continuously producing a viral antigen from a transformed cell infected with a virus according to claim 1, cells of said line being capable of continuously reproducing themselves for at least 25 passages and continuously produce viral antigen which comprises culturing cells of said cell line in fluid medium under conditions conducive to the production of said antigen to allow said antigen to be produced in the fluid medium harvesting, when required, an aliquot of said fluid medium and isolating said antigen from said aliquot to yield a purified antigen.

4. A method of continuously producing a bovine Maedi-Visna-like virus antigen from a Cf2Th cell line infected with bovine Maedi-Visna-like virus according to claim 2, cells of said cell line being capable of continuously reproducing themselves for at least 25 passages and continuously produce viral antigen which comprises culturing cells of said cell line in fluid medium under conditions conducive to the production of said antigen to allow said antigen to be produced in the fluid medium harvesting, when required, an aliquot of said fluid medium and isolating said antigen from said aliquot to yield a purified antigen.

5. A method according to claim 3 wherein said fluid medium comprises horse serum.

6. A method according to claim 3 wherein said fluid medium comprises fetal bovine serum.

7. A method according to claim 3 wherein said fluid medium is serum free.